United States Patent [19]
Johnson

[11] 4,094,988
[45] June 13, 1978

[54] METHOD OF TREATING GASTRIC ULCERS USING 5,6-DIHYDRO-1,4-DITHIINOXIDES

[75] Inventor: Richard C. Johnson, Ambler, Pa.

[73] Assignee: Warren-Teed Laboratories, Inc., Columbus, Ohio

[21] Appl. No.: 731,153

[22] Filed: Oct. 12, 1976

[51] Int. Cl.$^2$ .......................................... A61K 31/385
[52] U.S. Cl. .................................................... 424/277
[58] Field of Search ..................... 424/277; 260/327 P

[56] References Cited

U.S. PATENT DOCUMENTS

| | | | |
|---|---|---|---|
| 3,755,362 | 8/1973 | Asinger et al. | 260/327 P |
| 3,855,240 | 12/1974 | Mueller | 260/327 P |
| 3,920,438 | 11/1975 | Brewer | 260/327 P |

*Primary Examiner*—Frederick E. Waddell
*Attorney, Agent, or Firm*—Marion C. Staves

[57] ABSTRACT

5,6-Dihydro-1,4-dithiinoxides, compositions containing the 5,6-dihydro-1,4-dithiinoxides as their active ingredient and methods useful in the treatment of gastric ulcers are disclosed.

7 Claims, No Drawings

METHOD OF TREATING GASTRIC ULCERS USING 5,6-DIHYDRO-1,4-DITHIINOXIDES

This invention relates to 5,6-dihydro-1,4-dithiinoxides, compositions containing 5,6-dihydro-1,4-dithiinoxides as the active ingredient and methods of treatment of gastric ulcers.

Pharmacological studies employing rats as the experimental animal indicate that the products and compositions containing the active products are effective antisecretory and antiulcer agents useful in treating gastric ulcers.

In accordance with the present invention, there are employed in the compositions for treating gastric ulcers an active ingredient having the formula:

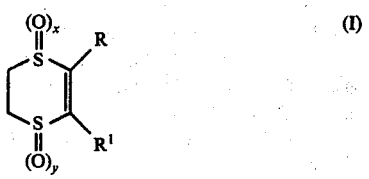

wherein R is alkyl, for example, lower alkyl having from 1 to 6 carbon atoms such as methyl, ethyl, n-propyl, sec-butyl, sec-propyl, sec-butyl, tert-butyl, pentyl, hexyl and the like or mononuclear aryl such as phenyl and the like; $R^1$ is alkyl, for example, lower alkyl of from 1 to 6 carbon atoms, such as methyl, ethyl, propyl, butyl, pentyl, hexyl and the like and $x$ and $y$ are integers each having a value of 0 to 2 with the sum of the integers $x$ and $y$ being in the range of from 1 to 4.

The preferred embodiment of this invention relates to the 5,6-dihydro-1,4-dithiin-1,1,4,4-tetroxides of the following formula:

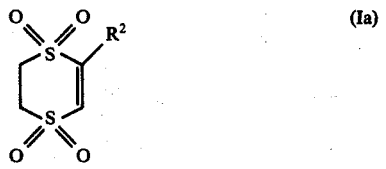

wherein $R^2$ is propyl or iso-propyl. The composition containing this class of compounds exhibits particularly good antisecretory/antiulcer activity and represents a preferred subgroup of compositions within the scope of this invention.

The compositions containing the 5,6-dihydro-1,4-dithiinoxides as the active ingredient and also the 5,6-dihydro-1,4-dithiinoxides (I) themselves are antiulcer agents which can be administered in a wide variety of therapeutic dosages in conventional vehicles, for example, by oral administration in the form of a tablet or capsule or oral solutions or suspensions. The pH of the aqueous solutions is preferably neutral or acidic. Also, the daily dosage of the products may be varied over a wide range varying from 10 to 150 milligrams. The product preferably is administered in subdivided doses in the form of scored tablets containing 5, 10, 25, 50, 100, 150, 250 and 500 milligrams of the active ingredient for the symptomatic adjustment of the dosage to the patient to be treated. An effective amount of the drug is ordinarily supplied at a dosage level of from about 1 mg. to about 10 mg./kg. Preferably, the range is from about 1 mg. to about 5 mg./kg. of body weight. These dosages are well below the toxic or lethal dose of the products.

A suitable unit dosage form of the products of this invention can be administered by mixing 50 mg. of a 5,6-dihydro-1,4-dithiin-oxide with 149 mg. of lactose and 1 mg. of magnesium stearate and placing the 200 mg. mixture into a No. 1 gelatin capsule. Similarly, by employing more of the active ingredient and less lactose, other dosage forms can be put up in No. 1 gelatin capsules, should it be necessary to mix more than 200 mg. of ingredient together, larger capsules may be employed. Tablets may be prepared by mixing the active ingredient with conventional tabletting ingredients, such as calcium phosphate, lactose, corn starch or magnesium stearate. The liquid forms in which the active ingredients may be incorporated include suitably flavored suspending or dispersing agents, such as the synthetic and natural gums, for example, tragacanth, acacia, methyl cellulose and the like. Other dispersing agents which may be employed include glycerin and the like.

It is also within the scope of this invention to combine two or more of the compounds of this invention in a unit dosage form or to combine one or more of the compounds of this invention with known antiulcer agents or with other desired therapeutic and/or nutrative agents in dosage unit form.

The 1,4-dithiinoxides are either known compounds or may be prepared by the reaction disclosed in U.S. Pat. No. 3,920,438 which patent is hereby incorporated by reference. By employing milder oxidizing conditions the mono-, di-and trioxides can be prepared and isolated. For example, by using sodium meta-periodate, the 1 and 4 oxides may be obtained.

The following examples are illustrative of how to prepare various compositions containing the active ingredients of this invention. However, said examples are merely illustrative and should not be construed as limiting the scope of this invention.

EXAMPLE A

Tablets containing 100 mg. of active ingredient per tablet.

|  | Per Tablet |
| --- | --- |
| 2-(2'-propyl)-5,6-dihydro-1,4-dithiin 1,1,4,4-tetroxide | 100 mg. |
| Calcium Phosphate | 40 mg. |
| Lactose | 38 mg. |
| Corn Starch | 20 mg. |
| Magnesium Stearate | 2 mg. |
|  | 200 mg. |

The 2-(2'-propyl)-5,6-dihydro-1,4-dithiin-1,1,4,4-tetroxide is mixed with the calcium phosphate and lactose for 10 minutes and then passed through a mill to reduce the particle size. The combined ingredients are remixed for 5 minutes and corn starch is passed through a No. 60 sieve (U.S. Sieve Series) onto the ingredients. The combined ingredients are again remixed for 5 minutes and then magnesium stearate is added through a No. 60 sieve. After remixing for two minutes the ingredients are compressed into tablets.

EXAMPLE B

Oral Elixir Dosage Form containing 100 mg. of active ingredient per five ml.

| | Per 5 ml. |
|---|---|
| 2-n-propyl-5,6-dihydro-1,4-dithiin-1,1,4,4-tetroxide | 100 mg. |
| Sugar | 1.25 g. |
| Glycerin | 0.50 ml. |
| Ethyl Alcohol | 0.50 ml. |
| Sorbic Acid | 5.0 mg. |
| Sodium Bisulfite | 0.05 g. |
| Tartrazine | 0.20 mg. |
| Disodium Edetate | 0.0025 g. |
| Flavoring Agent | 0.01 ml. |
| Purified Water USP | q$^s$ |

The following procedure is conducted under a nitrogen atmosphere. The sugar is dissolved in purified water. Glycerin is added followed by the addition of sodium bisulfite and disodium edetate in an equal quantity of purified water. An ethanolic solution is 2-n-propyl-5,6-dihydro-1,4-dithiin-1,1,4,4-tetroxide and sorbic acid is then added. To this solution is added an aqueous solution of tartrazine followed by the addition of the flavoring agent. Sufficient water is added to bring to final volume. The solution is stirred for 5 minutes, allowed to age overnight and filtered.

EXAMPLE C

Oral Suspension Dosage Form containing 100 mg. of active ingredient per 5 ml.

| | Per 5 ml. |
|---|---|
| 2,3-Dimethyl-5,6-dihydro-1,4-dithiin-1,1,4,4-tetroxide | 100 mg. |
| Vegetable Gum | 15.0 mg. |
| Tragacanth | 15.0 mg. |
| Sorbic Acid | 5.0 mg. |
| Sodium Bisulfite | 0.05 g. |
| Dimethicone | 0.15 mg. |
| Disodium Edetate | 0.0025 g. |
| Ethyl Alcohol | 0.05 ml. |
| Tartrazine | 0.25 mg. |
| Sorbitol Solution USP | 2.50 ml. |
| Flavoring Agent | 0.005 ml. |
| Purified Water USP | q$^s$ |

The following procedure is conducted under a nitrogen atmosphere. After hydrating the tragacanth in purified water overnight the sorbitol solution is added. Sorbic acid in ethyl alcohol and sodium bisulfite and disodium edetate in an equal quantity of purified water are then successively added. After adding the antifoam agent, dimethicone, in an equal quantity of water the 2,3-dimethyl-5,6-dihydro-1,4-dithiin-1,1,4,4-tetroxide is added. The tartrazine is dissolved in an equal quantity of purified water and is added followed by the addition of a suitable flavoring agent. The suspension is brought to its final volume with purified water, stirred for 5 minutes and then passed through an homogenizer.

EXAMPLE D

Dry-filled capsules containing 50 mg. of active ingredient per capsule.

| | Per Capsule |
|---|---|
| 2-Ethyl-3-n-propyl-5,6-dihydro-1,4-dithiin-1,1,4,4-tetroxide | 50 mg. |
| Lactose | 149 mg. |
| Magnesium Stearate | 1 mg. |
| | 200 mg. |

The 2-ethyl-3-n-propyl-5,6-dihydro-1,4-dithiin-1,1,4,4-tetroxide is reduced to a No. 60 powder and then lactose and magnesium stearate are passed through a No. 60 bolting cloth onto the powder and the combined ingredients admixed for 10 minutes and then filled into a No. 1 dry gelatin capsule.

Similar dry-filled capsules, tablets, elixirs and suspensions can be prepared by replacing the active ingredients of the above examples by any of the other compounds described in the foregoing general disclosure and the specific examples which follow.

EXAMPLE 1

2-(2'-Propyl)-5,6-dihydro-1,4-dithiin-1,1,4,4-tetroxide

Step A —
2-Ethoxycarbonylmethyl-2-(2'-propyl)-1,3-dithiolane

Ethyl isobutyrylacetate (49.6 g.), ethane-1,2-dithiol (28 ml.), polysulfonic acid resin (1.0 g.) and benzene (100 ml.) are heated at reflux until the rate of water collection in a Dean-Stark trap becomes slow (4.5 hours). The solution is allowed to cool and the catalyst is removed by filtration. The solvent is removed by distillation and the residual oil is distilled through a simple head at reduced pressure to afford 2-ethoxycarbonylmethyl-2-(2'-propyl)-1,3-dithiolane (60 g.; b.p. 92° C./0.10 mm.)

Elemental analysis for $C_{10}H_{18}O_2S_2$ Calc.: C, 51.27; H, 7.74; S, 27.36 Found: C, 50.99; H, 7.76; S, 27.52

STEP B —
3-Ethoxycarbonyl-2-(2'-propyl)-5,6-dihydro-1,4-dithiin

Sulfuryl chloride (18.0 ml.) in solution with methylene chloride (25 ml.) is added with efficient stirring to a solution of 2-ethoxycarbonylmethyl-2-(2'-propyl)-1,3-dithiolane (49.0 g.) in methylene chloride (300 ml.) at such a rate that the temperature does not exceed −70° C. (1 hour). When addition is complete, the resulting solution is stirred for one hour at < −65° C. and then allowed to warm to room temperature over 2.5 hours and left to remain overnight. Gaseous hydrogen chloride begins to be evolved at about −25° C. during the warming process and continues becoming vigorous (0°–10° C.). Residual hydrogen chloride is removed by washing with aqueous sodium bicarbonate solution and the product solution is dried over anhydrous sodium sulfate. Solvent is removed by distillation and the residual oil is distilled at reduced pressure to afford 3-ethoxycarbonyl-2-(2'-propyl)-5,6-dihydro-1,4-dithiin (42 g.), b. p. 114° C./0.2 mm.

Elemental analysis for $C_{10}H_{16}O_2S_2$ Calc.: C, 51.69; H, 6.94; S, 27.60 Found: C, 51.71; H, 7.02; S, 27.84

STEP C —
2-Carboxy-3-(2'-propyl)-5,6-dihydro-1,4-dithiin

3-Ethoxycarbonyl-2-(2'-propyl)-5,6-dihydro-1,4-dithiin (21.4 g.) is heated at reflux for 8 hours in a solution of potassium hydroxide (85%; 6.27 g.) in ethanol (75 ml.). The cool solution is acidified with aqueous hydrochloric acid and the precipitate is removed by filtration and dried (16.2 g.). The crude product is recrystallized from aqueous methanol to afford 2-carboxy-3-(2'-propyl)-5,6-dihydro-1,4-dithiin (m.p. 109.5°–113° C.).

Elemental analysis for $C_8H_{12}O_2S_2$ Calc.: C, 47.03; H, 5.92; S, 31.39 Found: C, 47.26; H, 6.13; S, 31.56

STEP D —
2-Carboxy-3-(2'-propyl)-5,6-dihydro-1,4-dithiin-1-oxide

A solution of sodium meta-periodate (16.7 g.) in water (165 ml.) is added in one portion with stirring to a solution of 2-carboxy-3-(2'-propyl)-5,6-dihydro-1,4-dithiin (15.2 g.) in methanol (1300 ml.). Solid begins to separate from solution within minutes. When thin layer chromatography indicates the absence of starting material (1–2 hours), the solid is removed by filtration and the filtrate is concentrated in vacuo. The concentrate is diluted with an equal volume of brine and the mixture is extracted with three portions of ethyl acetate. The combined extract is washed with dilute aqueous sodium bisulfite and brine and finally dried over anhydrous sodium sulfate. Removal of solvent in vacuo affords 2-carboxy-3-(2'-propyl)-5,6-dihydro-1,4-dithiin-1-oxide (13.2 g.; m.p. 194° C. dec.).

Elemental analysis for $C_8H_{12}O_3S_2$ Calc.: C, 43.61; H, 5.49; S, 29.11 Found: C, 43.56; H, 5.40; S, 29.21

STEP E —
2-(2'-Propyl)-5,6-dihydro-1,4-dithiin-1,1,4,4-tetroxide

Hydrogen peroxide (30% aqueous; 11.0 ml.) is added with stirring to a solution of 2-carboxy-3-(2'-propyl)-5,6-dihydro-1,4-dithiin-1-oxide (8.42 g.) in glacial acetic acid (86 ml.). The solution is placed in a water bath and left to stand at room temperature until reaction is complete as determined by thin layer chromatography (1–4 days). The solution is poured over ice and the solid product is removed by filtration (0.66 g.). The filtrate is concentrated in vacuo and the concentrate is diluted with an equal volume of brine. Extraction with ethyl acetate provides additional product (7.44 g.). Yield of 2-(2'-propyl)-5,6-dihydro-1,4-dithiin-1,1,4,4-tetroxide is 8.10 g. (m.p. 178.0°–179.0° C. from ethyl acetate heptane).

Elemental analysis for $C_7H_{12}O_4S_2$ Calc.: C, 37.48; H, 5.39; S, 28.59 Found: C, 37.22; H, 5.34; S, 28.75

EXAMPLE 2
2-n-Propyl-5,6-dihydro-1,4-dithiin-1,1,4,4-tetroxide

STEP A —
2-Ethoxycarbonylmethyl-2-n-propyl-1,3-dithiolane

By following substantially the procedure of Example 1, Step A, 2-ethoxycarbonylmethyl-2-n-propyl-1,3-dithiolane (273 g.; 87° C./0.07 mm.) is obtained from ethyl butyrylacetate (198 g.) and ethane-1,2-dithiol (120 ml.).

Elemental analysis for $C_{10}H_{18}O_2S_2$ Calc.: C, 51.27; H, 7.74; S, 27.36 Found: C, 50.94; H, 7.76; S, 27.03

STEP B —
3-Ethoxycarbonyl-2-n-propyl-5,6-dihydro-1,4-dithiin

By following substantially the procedure of Example 1, Step B, 2-ethoxycarbonylmethyl-2-n-propyl-1,3-dithiolane (248 g.) affords 3-ethoxycarbonyl-2-n-propyl-5,6-dihydro-1,4-dithiin (212 g.; b.p. 106° C./0.12 mm.).

Elemental analysis for $C_{10}H_{16}O_2S_2$ Calc.: C, 51.69; H, 6.94; S, 27.60 Found: C, 51.60; H, 7.14; S, 27.88

Step C — 2-Carboxy-3-n-propyl-5,6-dihydro-1,4-dithiin

By following substantially the procedure of Example 1, Step C, 3-ethoxycarbonyl-2-n-propyl-5,6-dihydro-1,4-dithiin (100 g.) was converted to 2-carboxy-3-n-propyl-5,6-dihydro-1,4-dithiin (87 g.; m.p. 105°–108° C.).

Elemental analysis for $C_8H_{12}O_2S_2$ Calc.: C, 47.03; H, 5.92; S, 31.39 Found: C, 46.96; H, 5.91; S, 31.41

STEP D —
2-n-Propyl-5,6-dihydro-1,4-dithiin-1,1,4,4-tetroxide

Hydrogen peroxide (35% aqueous; 9.1 ml.) as a solution in glacial acetic acid (10 ml.) is added by drops to an ice cooled (10° C.) solution of 2-carboxy-3-n-propyl-5,6-dihydro-1,4-dithiin (19.7 g.) in glacial acetic acid (210 ml.) and water (20 ml.). The resulting solution is kept at 10° C. or below overnight. Subsequently, an additional quantity of hydrogen peroxide (35 ml.) is added and the resulting solution is heated in a hot water bath (80° C. but no higher) for 1 hour. The progress of the reaction is followed by thin layer chromatography (tetroxide is the most mobile spot appearing ~Rf 0.7 using ethyl acetate/carbon tetrochloride 1:1) and additional heating or addition of more oxidizing agent determined accordingly. When the reaction is complete, excess solvent is removed under reduced pressure. The residual material is mixed with ice and the solid product is removed by filtration, washed with diluted aqueous sodium bisulfite solution, water, a small quantity of methanol and dried to afford 2-n-propyl-5,6-dihydro-1,4-dithiin-1,1,4,4-tetroxide (12.6 g.; m.p. 182.5°–183.5° C.).

Elemental analysis for $C_7H_{12}O_4S_2$ Calc.: C, 37.48; H, 5.39; S, 28.59 Found: C, 38.29; H, 5.15; S, 28.46

EXAMPLE 3
2-Ethyl-3-n-propyl-5,6-dihydro-1,4-dithiin-1,1,4,4-tetroxide and
2-(1'-chloroethyl)-3-n-propyl-5,6-dihydro-1,4-dithiin-1,1,4,4-tetroxide Step A — 2,2-Di-n-propyl-1,3-dithiolane By following substantially the procedure of Example 1, Step A, and by substituting 4-heptanone (113 g.) for ethyl isobutyrylacetate, there is obtained 2,2-di-n-propyl-1,3-dithiolane (184.5 g.; b.p. 75° C./0.3 mm.)

Elemental analysis for $C_9H_{18}S_2$ Calc.: C, 56.78; H, 9.53; S, 33.69 Found: C, 56.58; H, 9.49; S, 34.40

Step B — 2-Ethyl-3-n-propyl-5,6-dihydro-1,4-dithiin and
2-(1'-chloroethyl)-3-n-propyl-5,6-dihydro-1,4-dithiin By following substantially the procedure of Example 1, Step B, 2,2-di-n-propyl-1,3-dithiolane (95 g.) yields a mixture (determined by gas chromatography) of starting material (17%), 2-ethyl-3-n-propyl-5,6-dihydro-1,4-dithiin (69%) and 2-(1'-chloroethyl)-3-n-propyl-5,6-dihydro-1,4-dithiin (14%). The crude product (after processing) is distilled through a simple head at a reduced pressure collecting fractions boiling 62°–75° C./0.05 mm. (68 g.) and 90°–93° C./0.01 mm. (14.3 g.). The lower boiling fraction is redistilled through a 30 cm. column packed with monel chips to afford, after passage of fractions containing starting material (37 g.; b.p. 47°–51° C./0.05 mm.), 2-ethyl-3-n-propyl-5,6-dihydro-1,4-dithiin (20.8 g.; b.p. 52° C./0.05 mm.).

Elemental analysis for $C_9H_{16}S_2$ Calc.: C, 57.39; H, 8.56; S, 34.05 Found: C, 57.20; H, 8.62; S, 34.41

The fraction having b.p. 90°–93° C./0.01 mm. (vida supra) is redistilled through a 13 cm column packed with glass helices affording purified (87%) 2-(1'-chloroethyl)-3-n-propyl-5,6-dihydro-1,4-dithiin (7.0 g.; b.p. 92°–93° C./0.05 mm.).

Elemental analysis for $C_9H_{15}ClS_2$ Calc.: C, 48.52; H, 6.79; Cl, 15.91; S, 28.78 Found: C, 48.07; H, 6.96; Cl, 13.76; S, 28.68

Step C — 2-Ethyl-3-n-propyl-5,6-dihydro-1,4-dithiin-1-, and 4-oxides

By following substantially the procedure of Example 1, Step D, 2-ethyl-3-n-propyl-5,6-dihydro-1,4-dithiin (15.0 g.) yields 2-ethyl-3-n-propyl-5,6-dihydro-1,4-dithiinoxides as a mixture of the 1- and 4-isomers (viscous oil).

STEP D — 2-Ethyl-3-n-propyl-5,6-dihydro-1,4-dithiin-1,1,4,4-tetroxide

By following substantially the procedure of Example 1, Step E, 2-ethyl-3-n-propyl-5,6-dihydro-1,4-dithiin oxides (10.0 g.) yields 2-ethyl-3-n-propyl-5,6-dihydro-1,4-dithiin-1,1,4,4-tetroxide (11.0 g.; m.p. 105.5°–106.5° C.).

Elemental analysis for $C_9H_{16}O_4S_2$ Calc.: C, 42.84; H, 6.39; S, 25.41 Found: C, 42.34; H, 6.41; S, 24.80

STEP E — 2-(1'-Chloroethyl)-3-n-propyl-5,6-dihydro-1,4-dithiin-1- and 4-oxide By following substantially the procedure of Example 1, Step D, however, using dioxane as the solvent, 2-(1'-chloroethyl)-3-n-propyl-5,6-dihydro-1,4-dithiin (5.17 g.) yields 2-(1'-chloroethyl)-3-n-propyl-5,6-dihydro-1,4-dithiin oxides as a mixture of the 1-, and 4-isomers (5.55 g.).

STEP F — 2-(1'-Chloroethyl)-3-n-propyl-5,6-dihydro-1,4-dithiin-1,1,4,4-tetroxide By following substantially the procedure of Example 1, Step E, 2-(1'-chloroethyl)-3-n- propyl-5,6-dihydro-1,4-dithiin (5.0 g.) yields 2-(1'-chloroethyl)-3-n-propyl-5,6-dihydro-1,4-dithiin-1,1,4,4-tetroxide (4.52 g.; m.p. 103°–108° C.).

Elemental analysis for $C_9H_{15}ClO_4S_2$ Calc.: C, 37.69; H, 5.27; Cl, 12.36; S, 22.36 Found: C, 37.29; H, 5.14; Cl, 12.41; S, 22.50

EXAMPLE 4

2,3-Dimethyl-5,6-dihydro-1,4-dithiin-1,1,4,4-tetroxide

Step A — 2,3-Dimethyl-5,6-dihydro-1,4-dithiin

3-Bromo-2-butanone (97.4 g.) is added with stirring to a solution of ethane-1,2-dithiol (55.9 ml.) in benzene (600 ml.). Aqueous hydrogen bromide soon begins to separate out as a phase. The mixture is allowed to stand overnight. The aqueous phase is separated and the organic phase washed with aqueous sodium bicarbonate solution with final drying over anhydrous sodium sulfate. Solvent is removed and the product distilled under reduced pressure to afford 2,3-dimethyl-5,6-dihydro-1,4-dithiin (65 g.; b.p. 55°–57° C./0.1 mm.).

Elemental analysis for $C_6H_{10}S_2$ Calc.: C, 49.27; H, 6.89; S, 43.84 Found: C, 49.26; H, 7.03; S, 43.86

Step B — 2,3-Dimethyl-5,6-dihydro-1,4-dithiin-1-oxide

By following substantially the procedure of Example 1, Step D, 2,3-dimethyl-5,6-dihydro-1,4-dithiin (20.0 g.) yields 2,3-dimethyl-5,6-dihydro-1,4-dithiin-1-oxide (21.6 g.) as a viscous oil.

Elemental analysis for $C_6H_{10}OS_2.0.36\ H_2O$ Calc.: C, 42.69; H, 6.65; S, 37.58 Found: C, 42.69; H, 6.40; S, 37.99

STEP C — 2,3-Dimethyl-5,6-dihydro-1,4-dithiin-1,1,4,4-tetroxide

By following substantially the procedure of Example 1, Step E, 2,3-dimethyl-5,6-dihydro-1,4-dithiin-1-oxide (10.0 g.) yields 2,3-dimethyl-5,6-dihydro-1,4-dithiin-1,1,4,4-tetroxide (9.18 g.; m.p. 169.0°–170.5° C.).

Elemental analysis for $C_6H_{10}O_4S_2$ Calc.: C, 34.27; H, 4.79; S, 30.50 Found: C, 34.23; H, 4.67; S, 30.42

EXAMPLE 5

2-Phenyl-5,6-dihydro-1,4-dithiin-1,1,4,4-tetroxide

Step A — 2-Phenyl-5,6-dihydro-1,4-dithiin

By following substantially the procedure of Example 4, Step A, phenacyl bromide (95.0 g.) and ethane-1,2-dithiol (40.0 ml.) in benzene (500 ml.) is allowed to stand for 2 days at room temperature (until gas chromatography indicates the absence of starting material). Solid by-product is removed by filtration and the filtrate is washed with aqueous sodium bicarbonate solution and water. The product solution is dried over anhydrous sodium sulfate. Solvent is removed by distillation and the residual oil is distilled at reduced pressure to afford 2-phenyl-5,6-dihydro-1,4-dithiin (47.2 g.; b.p. 140°–150° C./0.25 mm.). The product solidifies on standing and is recrystallized from methanol (m.p. 58.0°–59.0° C.).

Elemental analysis for $C_{10}H_{10}S_2$ Calc.: C, 61.81; H, 5.19; S, 33.00 Found: C, 62.15; H, 5.30; S, 33.06

Step B — 2-Phenyl-5,6-dihydro-1,4-dithiin-1- and 4-oxides

By following substantially the procedure of Example 1, Step D, except using dioxane as solvent, 2-phenyl-5,6-dihydro-1,4-dithiin (14.0 g.) yields 2-phenyl-5,6-dihydro-1,4-dithiin oxide as a mixture of the 1- and 4-isomers (15.1 g.).

STEP C — 2-Phenyl-5,6-dihydro-1,4-dithiin-1,1,4,4-tetroxide

By following substantially the procedure of Example 1, Step E, 2-phenyl-5,6-dihydro-1,4-dithiin oxide (15.1 g.) yields 2-phenyl-5,6-dihydro-1,4-dithiin-1,1,4,4-tetroxide (13.2 g.; m.p. 203.5°–205.5° C.).

Elemental analysis for $C_{10}H_{10}O_4S_2$ Calc.: C, 46.51; H, 3.90; S, 24.83 Found: C, 46.45; H, 3.94; S, 24.89

What is claimed is:

1. A method of treating ulcers which comprises administering to a person in need of such treatment an effective amount of the compound of the formula:

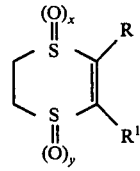

wherein R is lower alkyl having from one to 6 carbon atoms or phenyl; $R^1$ is lower alkyl of from 1 to 6 carbon atoms and $x$ and $y$ are integers each having a value of 0 to 2 with the sum of $x$ and $y$ being in the range of from 1 to 4.

2. The method of claim 1 wherein the active ingredient has the formula:

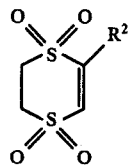

wherein R² is propyl or isopropyl.

3. The method of claim 1 wherein the active ingredient is 2-(2'-propyl)-5,6-dihydro-1,4-dithiin-1,1,4,4-tetroxide.

4. The method of claim 1 wherein the active ingredient is 2-n-propyl-5,6-dihydro-1,4-dithiin-1,1,4,4-tetroxide.

5. The method of claim 1 wherein the active ingredient is 2-ethyl-3-n-propyl-5,6-dihydro-1,4-dithiin-1,1,4,4-tetroxide.

6. The method of claim 1 wherein the active ingredient is 2,3-dimethyl-5,6-dihydro-1,4-dithiin-1,1,4,4-tetroxide.

7. The method of claim 1 wherein the active ingredient is 2-phenyl-5,6-dihydro-1,4-dithiin-1,1,4,4-tetroxide.

* * * * *